(12) United States Patent
Park

(10) Patent No.: US 10,350,357 B2
(45) Date of Patent: Jul. 16, 2019

(54) DRUG INJECTION DEVICE

(71) Applicant: MEGAGEN IMPLANT CO., LTD., Gyeongsan-si, Gyeongsangbuk-do (KR)

(72) Inventor: Kwang Bum Park, Daegu (KR)

(73) Assignee: MEGAGEN IMPLANT CO., LTD. (KR)

(*) Notice: Subject to any disclaimer, the term of this patent is extended or adjusted under 35 U.S.C. 154(b) by 243 days.

(21) Appl. No.: 15/035,221

(22) PCT Filed: Nov. 4, 2014

(86) PCT No.: PCT/KR2014/010511
§ 371 (c)(1),
(2) Date: May 6, 2016

(87) PCT Pub. No.: WO2015/069004
PCT Pub. Date: May 14, 2015

(65) Prior Publication Data
US 2016/0271329 A1  Sep. 22, 2016

(30) Foreign Application Priority Data
Nov. 7, 2013 (KR) .......... 10-2013-0135079

(51) Int. Cl.
A61M 5/20 (2006.01)
A61M 5/24 (2006.01)
A61M 5/315 (2006.01)
A61M 5/31 (2006.01)

(52) U.S. Cl.
CPC .......... *A61M 5/31511* (2013.01); *A61M 5/20* (2013.01); *A61M 5/24* (2013.01);
(Continued)

(58) Field of Classification Search
CPC ...... A61M 5/3148; A61M 2005/31588; A61M 2205/8206; A61M 5/31583; A61M 5/24;
(Continued)

(56) References Cited

U.S. PATENT DOCUMENTS 4,758,234 A * 7/1988 Orentreich ............ A61M 5/24
604/232
5,624,400 A * 4/1997 Firth .................... A61M 5/3243
604/110
(Continued)

FOREIGN PATENT DOCUMENTS

CN 1572333 A 2/2005
CN 101282756 A 10/2008
(Continued)

*Primary Examiner* — Brandy S Lee
*Assistant Examiner* — William R Frehe
(74) *Attorney, Agent, or Firm* — Renaissance IP Law Group LLP

(57) ABSTRACT

A drug injection device is disclosed. A drug injection device, according to the present invention, comprises: a plunger which is connected to an ampoule filled with an injectable solution and applies pressure to the injectable solution in the ampoule; a manual plunger handle which is connected to one side of the plunger and manually applies pressure to the plunger; and an automatic plunger pressurizing unit which is selectively connected to the plunger in a position adjacent to same and automatically applies pressure to same by means of power.

11 Claims, 12 Drawing Sheets

(52) U.S. Cl.
CPC ....... *A61M 5/3148* (2013.01); *A61M 5/31583* (2013.01); *A61M 2005/3139* (2013.01); *A61M 2005/31588* (2013.01); *A61M 2205/8206* (2013.01)

(58) Field of Classification Search
CPC .............. A61M 5/3135; A61M 5/3137; A61M 2005/3139; A61M 5/31578; A61M 5/31581
See application file for complete search history.

(56) References Cited

U.S. PATENT DOCUMENTS

| | | | | |
|---|---|---|---|---|
| 6,159,161 | A * | 12/2000 | Hodosh | A61M 5/20 600/561 |
| 2004/0249344 | A1 | 12/2004 | Nemoto et al. | |
| 2011/0071393 | A1 | 3/2011 | Liu et al. | |
| 2012/0258421 | A1 * | 10/2012 | Selvitelli | A61M 5/19 433/90 |
| 2015/0151102 | A1 * | 6/2015 | Arduini | A61M 1/282 604/29 |
| 2016/0089497 | A1 * | 3/2016 | Fojtik | A61M 5/3137 604/227 |

FOREIGN PATENT DOCUMENTS

| | | |
|---|---|---|
| CN | 102218176 A | 10/2011 |
| CN | 102740908 A | 10/2012 |
| JP | 2011234774 A | 11/2011 |
| JP | 2013521083 | 6/2013 |
| KR | 101282666 | 7/2013 |
| WO | 9720588 A1 | 6/1997 |
| WO | 2007002053 A2 | 1/2007 |
| WO | 2011139110 A2 | 11/2011 |
| WO | 2013045617 A1 | 4/2013 |

* cited by examiner

DRUG INJECTION DEVICE

TECHNICAL FIELD

The present invention relates to a drug injection device, and more particularly, to a drug injection device capable of enhancing convenience by using the drug injection device manually and automatically and reducing a drug injection time by freely selecting an injection method according to sensitivity of a patient to improve satisfaction of the patient.

BACKGROUND ART

An implant means a substitute that recovers original human tissue when the original human tissue is lost, but indicates a series of operations that implants an artificially made tooth in the dentist.

When the implant is described in brief, the implant is an operation that implants a fixture which is a root of the tooth made of titanium without a rejection response to a human body, and the like in an alveolar bone which the tooth leaves so as to substitute for the lost tooth root and thereafter, fixes the artificial tooth to restore a function of the tooth.

The implant operation is diversified according to a type of the fixture, but is generally completed by punching an insertion location by using a predetermined drill and thereafter, inserts the fixture in the tooth bone and osseointegrates the fixture to a bone and couples an abutment to the fixture and thereafter, covers the abutment with a final prosthesis.

Neighbor teeth and bones of a general prosthesis or denture are emaciated, but the implant does not emaciate an adjacent dental tissue and has the same function or shape as a natural tooth and does not cause a decayed tooth, and as a result, the implant can be semipermanently used.

Further, the implant operation recovers a single lost tooth and promotes a function of the denture for patients having no partial tooth and complete tooth, enhances an aesthetic aspect of recovery of tooth prosthesis, distributes excessive stress applied to a neighbor supporting bone tissue and assists stabilization of a set of teeth.

Meanwhile, the implant operation performs gum incision, the punching by the drill, and the like during the operation to cause a lot of pains to a person being operated on. Therefore, in the implant operation, local anesthesia of an operation portion is required.

The local anesthesia is generally performed by pressing an anesthesia solution with a syringe to inject the anesthesia solution in the operation portion. In this case, when an injection speed of the anesthesia solution, that is, a pressing speed of the anesthesia solution is high, excessive pressure is generated at an injection portion of the anesthesia solution, and as a result, the person being operated on feels a pain.

Accordingly, the anesthesia solution needs to be injected as slow as possible. However, when the injection speed of the anesthesia solution decreases, an injection time of the anesthesia solution increases, consequently, a time when the operator holds the syringe increases.

When the time for which the operator holds the syringe increases, it is difficult for the operator to maintain a constant injection speed and the operated person feels the pain due to a hand vibration phenomenon. Therefore, a time for which the patient needs to open a mouth thereof increases and moreover, the person being operated on feels the pain due to the hand vibration phenomenon of the operator.

A lot of attempts have been made in order to solve the problem and as a representative example, an auto anesthesia apparatus disclosed in Korean Patent Registration No. 10-0784931 has been developed.

It is disclosed that the auto anesthesia apparatus has an advantage in that the injection speed of the anesthesia solution is appropriately controlled depending on a change in pressure formed at a portion to be operated to minimize the pain which the patient feels.

However, the drug injection apparatus having the structure has a disadvantage in that the structure of the drug injection apparatus is complicated and heavy, and as a result, it is hard for the operator to hold the drug injection apparatus for a long time and an additional pain by the hand vibration phenomenon is generated.

Meanwhile, when the anesthesia solution is inserted into a blood vessel during the local anesthesia, the pain is caused, and as a result, a syringe needs is inserted before the anesthesia solution is injected and thereafter, aspiration for verifying that the syringe needle does not penetrate the blood vessel by slightly pulling a syringe plunger back is performed or injecting the anesthesia solution by switching the auto injection apparatus to a manual mode under determination of the operator according to sensitivity or an anesthesia degree of the patient may be more convenient than automatically injecting the anesthesia solution.

However, as described above, since the auto anesthesia apparatuses in the related art are complicate in terms of the structures thereof and heavy, it is difficult for the operator to hold the auto anesthesia apparatuses for a long time and it is impossible to inject the anesthesia solution by switching the auto anesthesia apparatuses to the manual mode as necessary.

DISCLOSURE

Technical Problem

The present invention is directed to provide a drug injection device capable of enhancing convenience by using the drug injection device manually and automatically and reducing a drug injection time by freely selecting an injection method according to sensitivity of a patient to improve satisfaction of the patient.

Technical Solution

An aspect of the present invention provides a drug injection device, comprises: a plunger which is connected to an ampoule filled with an injectable solution and applies pressure to the injectable solution in the ampoule; a manual plunger handle which is connected to one side of the plunger and manually applies pressure to the plunger; and an automatic plunger pressurizing unit which is selectively connected to the plunger in a position adjacent to the plunger and automatically applies pressure to the plunger by means of power.

The automatic plunger pressurizing unit may comprise: a plunger driving portion which provides the power for applying the pressure to the plunger; a connection gear portion which is selectively connected to or released from the plunger by a gear method; and a gear operating portion which operates the connection gear portion.

The connection gear portion may comprise: a worm gear which is attached to the plunger driving portion; and a rack gear which is formed on an outer surface of the plunger and gear-engages with the worm gear.

The automatic plunger pressurizing unit may further comprise a unit casing which integrally supports the plunger driving portion and the worm gear.

The gear operating portion may comprise: a pusher which operates the unit casing so that the worm gear gear-engages with the rack gear when sliding pressure is applied in one direction; and an elastic member which is connected to the unit casing and elastically biased in a direction in which the worm gear is released from the rack gear.

The unit casing may include a slope contact portion formed on one surface facing the pusher, which is obliquely provided in a sliding direction of the pusher, and the pusher may comprise: a pressurizing member which applies pressure to the unit casing while sliding along the slope contact portion; and a pusher switch which is pin-connected to the pressurizing member.

A cut portion for exposing the worm gear in which the worm gear is exposed may be further formed in the unit casing.

The drug injection device may further comprise a plunger guide body which provides a plunger tunnel portion guided while the plunger is passed and is foldably attached with the unit casing.

A cut portion for exposing the rack gear in which the rack gear is exposed may be further formed in the plunger tunnel portion.

The drug injection device may further comprise a power supply unit which is accommodated in a bracket protruding on an outer wall of the plunger guide body to supply power to the plunger driving portion, in which the power supply unit may comprise: at least one charging battery supplying the power; and a compliance module which charges the at least one charging battery wiredly or wirelessly.

The drug injection device may further comprise a protection casing which protects the plunger guide body and the automatic plunger pressurizing unit at the outer sides of the plunger guide body and the automatic plunger pressurizing unit.

The manual plunger handle may comprise: a handle gripping portion which is attached to the outer wall of the protection casing to have a closed-loop shape and provided with a passing hole through which the plunger passes in a movement direction of the plunger; and a plunger pressurizing portion which is connected to one end of the plunger through the passing hole and applies the pressure to the plunger.

An insertion groove to which the handle gripping portion is inserted may be formed on the outer wall of the protection casing and an insertion projection which is inserted to the insertion groove may be provided on the handle gripping portion.

The drug injection device may further comprise an ampoule holder portion which is accommodated with the ampoule of the injectable solution and inserted into the protection casing, in which the ampoule holder portion may comprise: an ampoule accommodation portion in which the ampoule of the injectable solution is accommodated; a needle holder which is attached to the ampoule accommodation portion; and an intra-injection needle which is attached to the needle holder, and the ampoule accommodation portion may be provided with at least one locking projection which is projected in a circumferential direction in a position adjacent to the end portion of the ampoule accommodation portion, and when the ampoule accommodation portion rotates, the locking projection interferes in an interference wall formed in the protection casing.

The protection casing may comprise: an upper casing; and a lower casing which is assembled with the upper casing, and a projection portion which is projected in a circumferential direction may be provided at the upper casing and the outer side of the front end of the lower casing, the protection casing may further comprise a clamping cap which clamps the upper casing and the lower casing, and a groove portion which is dented in a circumferential direction to engage with the projection portion may be provided at the inside of the clamping cap.

Advantageous Effects

According to the present invention, it is possible to enhance convenience by using the drug injection device manually and automatically and reduce a drug injection time by freely selecting an injection method according to sensitivity of a patient to improve satisfaction of the patient.

MODES OF THE INVENTION

In order to sufficiently understand an operating advantage of the present invention and an object achieved by the present invention and exemplary embodiments of the present invention, the accompanying drawings illustrating the exemplary embodiments of the present invention and contents disclosed in the accompanying drawings should be referred.

Hereinafter, the exemplary embodiments of the present invention are described with reference to the accompanying drawings to describe the present invention in detail. However, in describing the present invention, a detailed description of already known functions or configurations will be omitted so as to make the subject matter of the present invention clear.

Prior to the description compared with the drawings, as an injection liquid to be described below, any one of various drugs injected into an animal or human body may be used.

However, the exemplary embodiment will exemplify an anesthetic solution for local anesthesia in a dental implant procedure.

Figure 1:
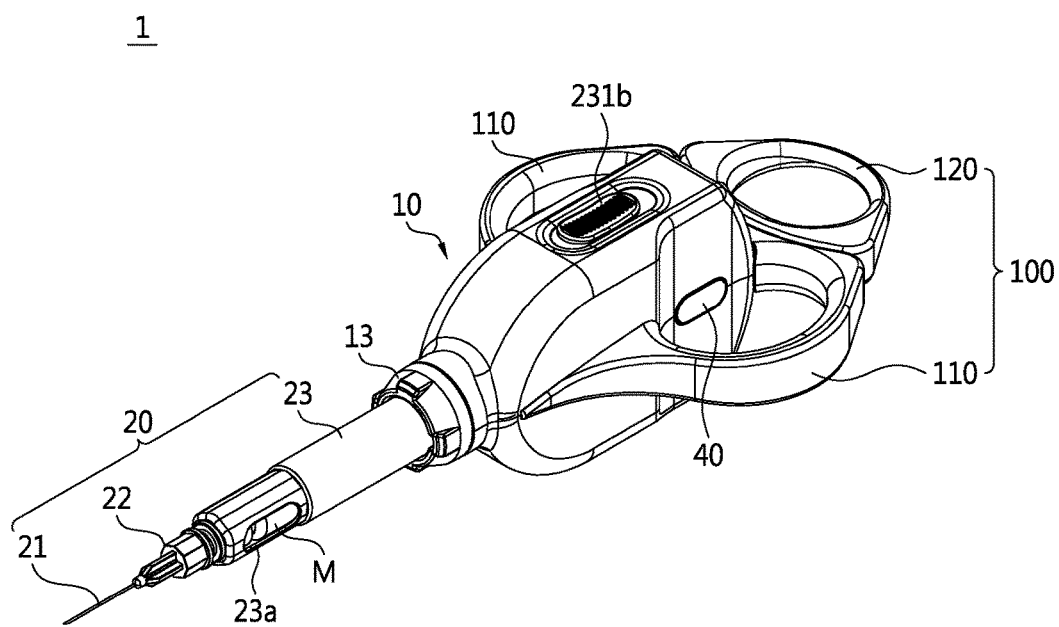
FIG. 1 is a perspective view illustrating a drug injection device according to an exemplary embodiment of the present invention.
Figure 2:
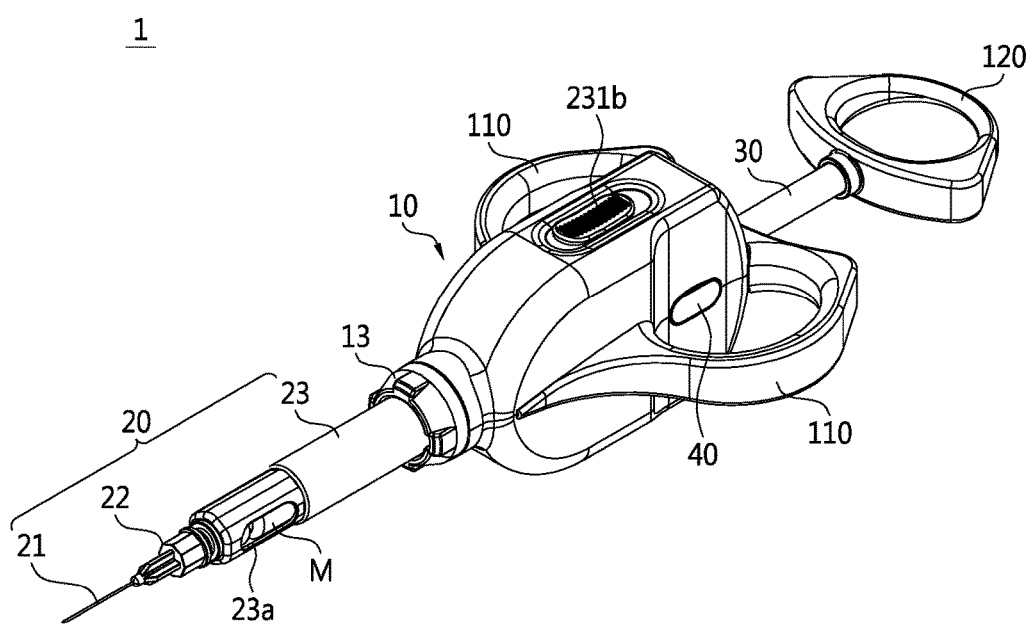
FIG. 2 is a diagram illustrating a state in which a plunger pressurizing portion in FIG. 1 is drawn back to a protection casing.
Figure 3:
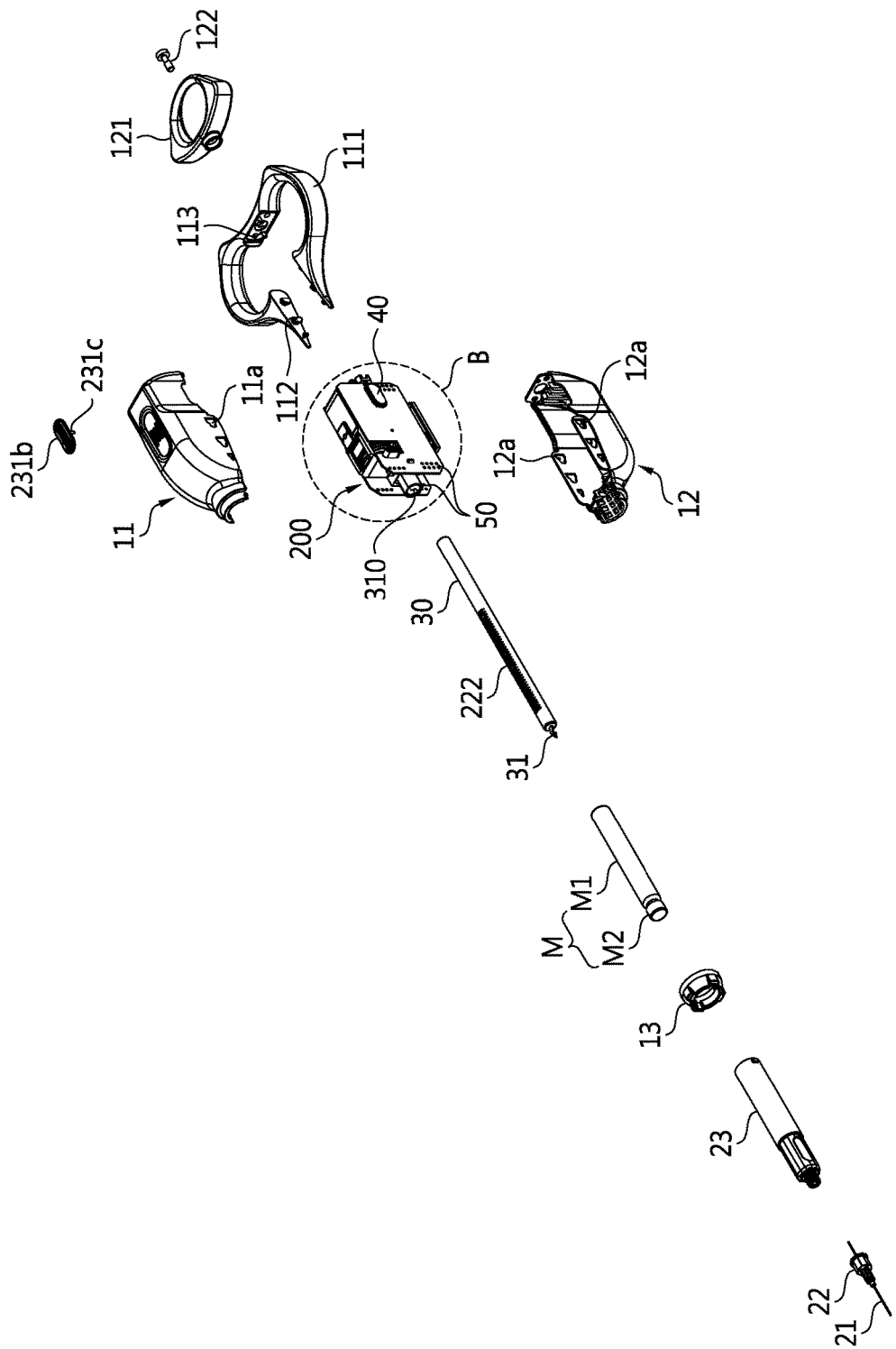
FIG. 3 is a partially exploded perspective view of the drug injection device of FIG. 1.
Figure 4:
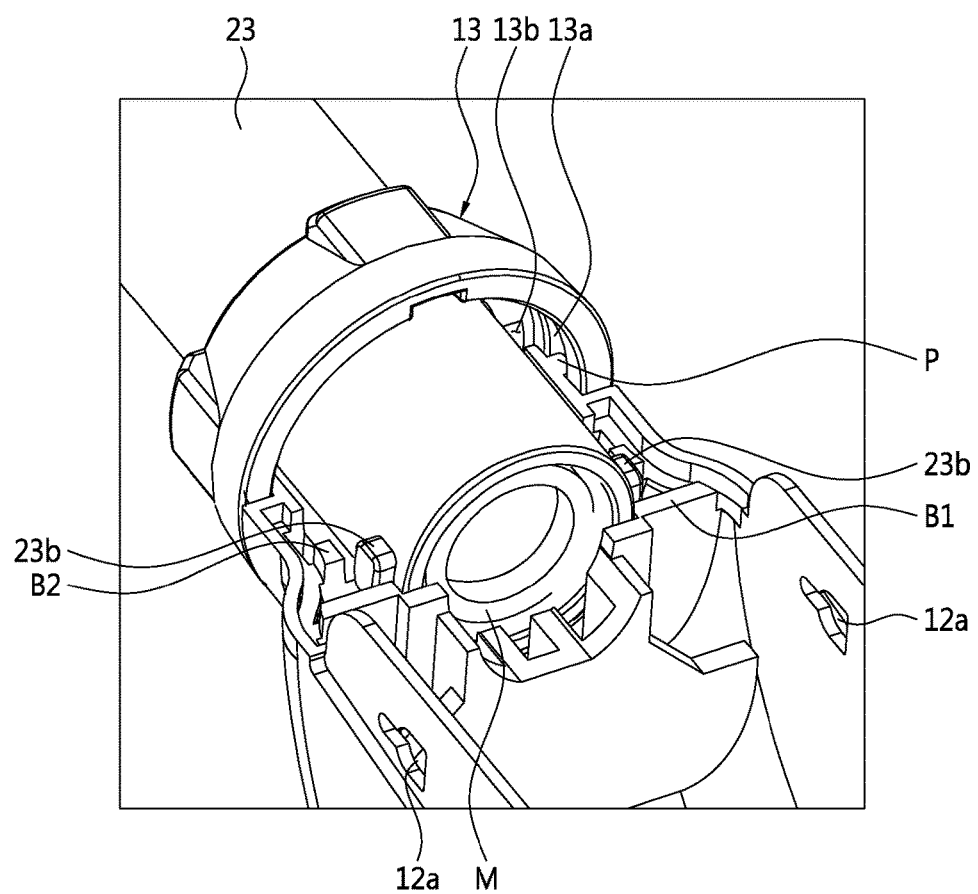
FIG. 4 is a partially cut enlarged diagram for describing a state in which an ampoule accommodation portion is installed in the protection casing in FIG. 1.
Figure 5:
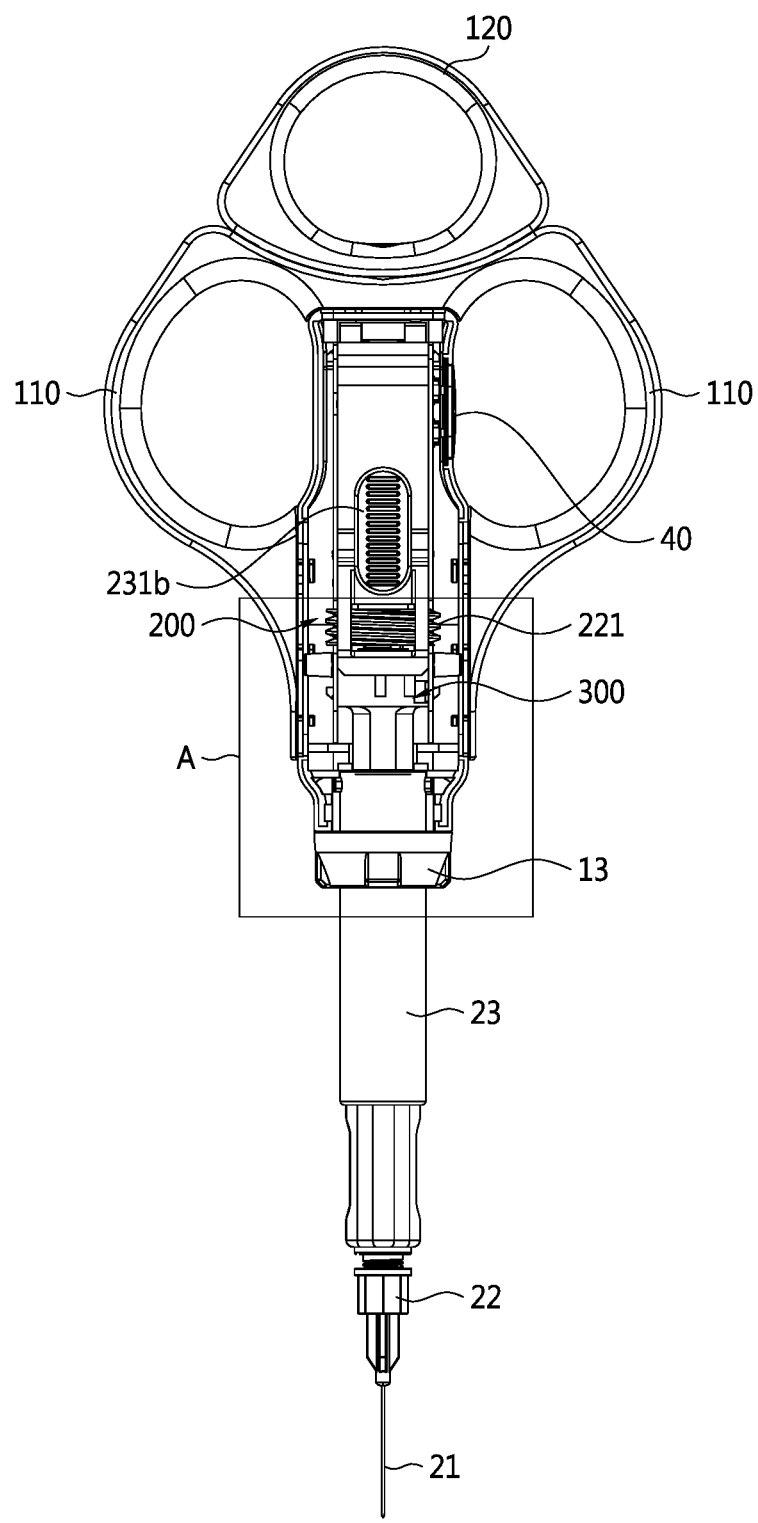
FIG. 5 is a plan view illustrating that an upper casing is removed in FIG. 1.
Figure 6:
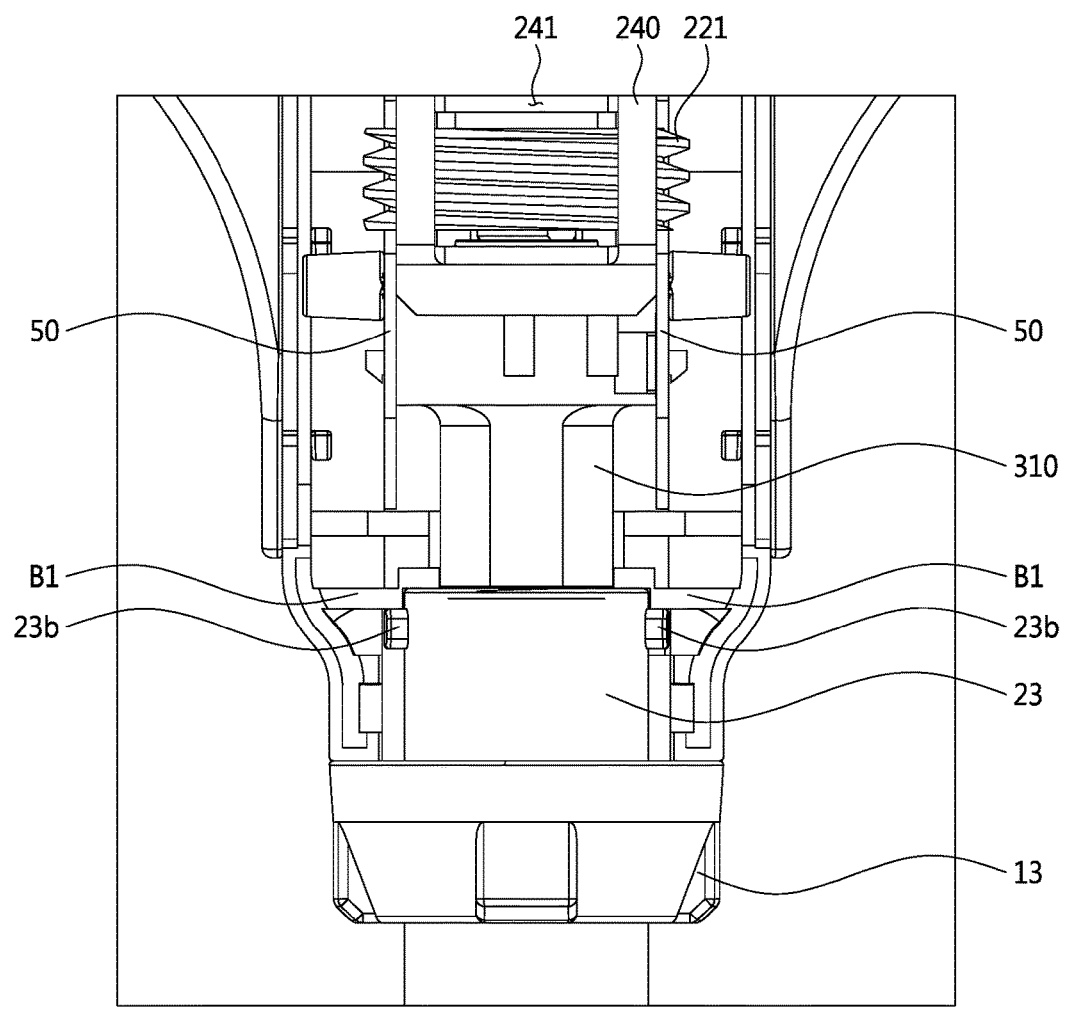
FIG. 6 is an enlarged diagram of region A of FIG. 5.
Figure 7:
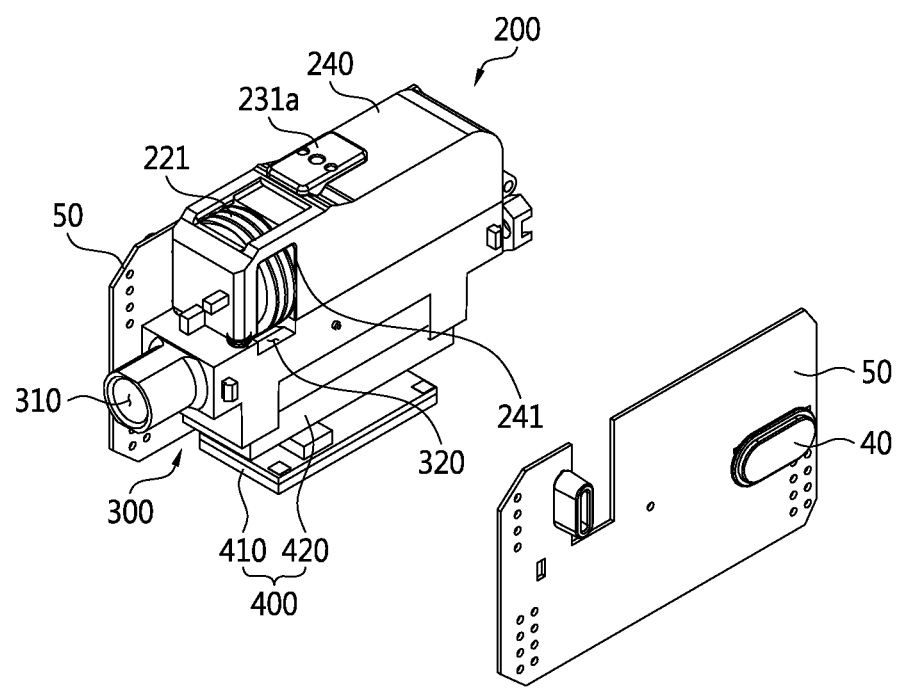
FIG. 7 is an enlarged diagram of region B of FIG. 3.
Figure 8:
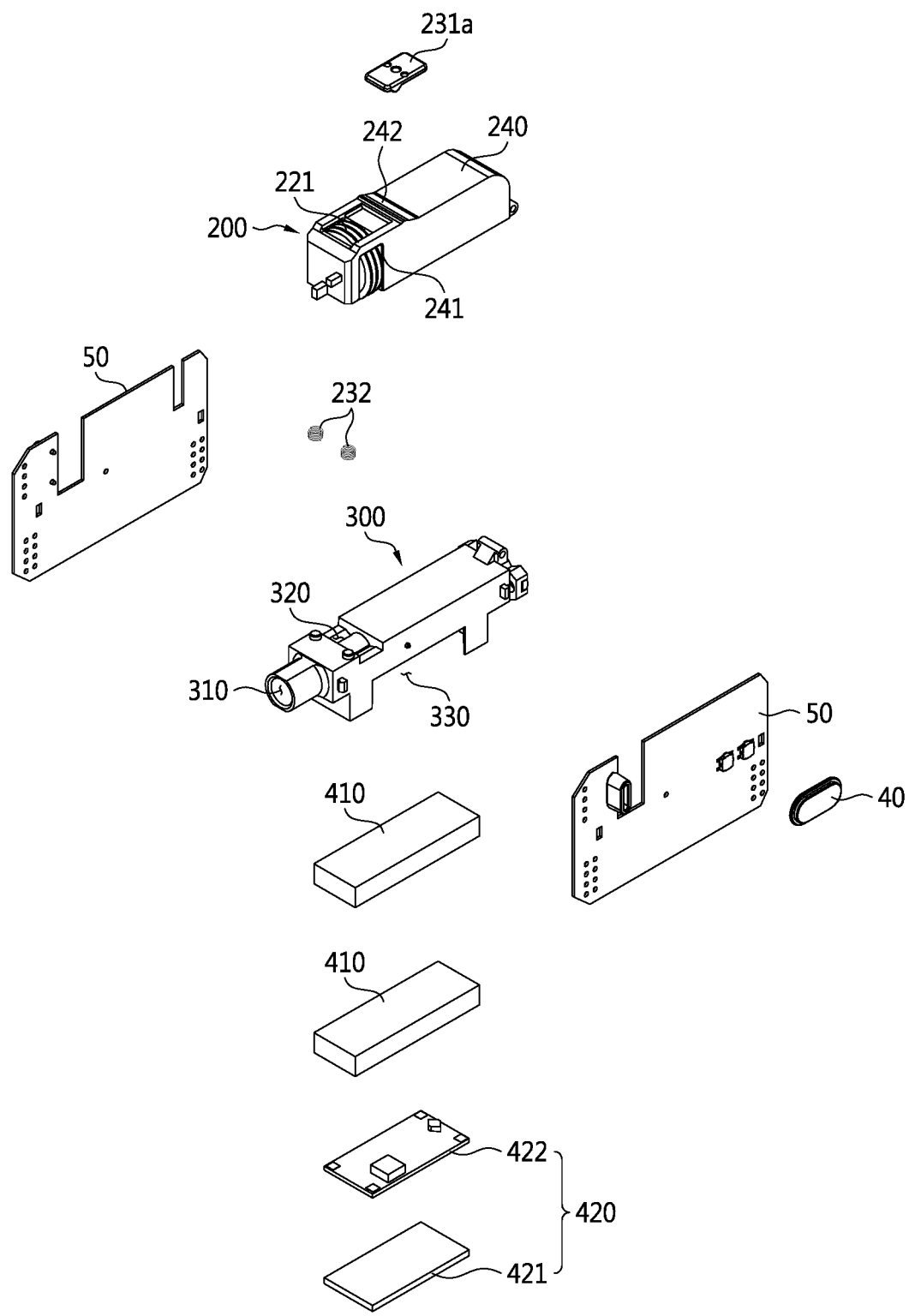
FIG. 8 is an exploded perspective view of FIG. 7.
Figure 9:
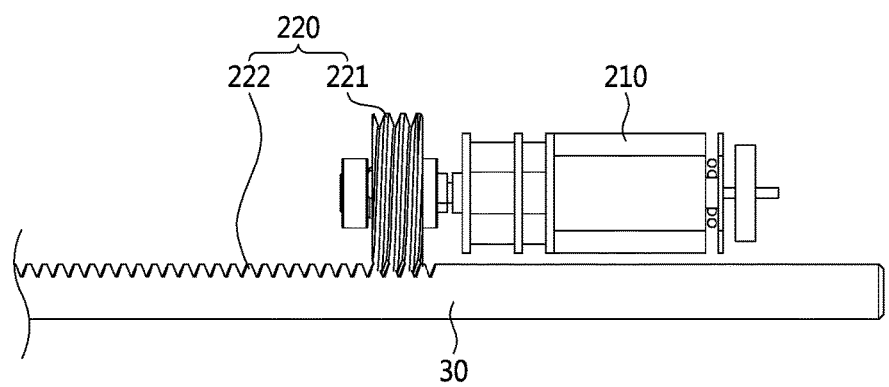
FIGS. 9 to 12 are reference diagrams for describing an operational mechanism of an automatic plunger pressurizing unit according to the exemplary embodiment of the present invention.

FIG. 1 is a perspective view illustrating a drug injection device according to an exemplary embodiment of the present invention, FIG. 2 is a diagram illustrating a state in which a plunger pressurizing portion in FIG. 1 is drawn back to a protection casing, FIG. 3 is a partially exploded perspective view of the drug injection device of FIG. 1, FIG. 4 is a partially cut enlarged diagram for describing a state in which an ampoule accommodation portion is installed in the protection casing in FIG. 1, FIG. 5 is a plan view illustrating that an upper casing is removed in FIG. 1, FIG. 6 is an enlarged diagram of region A of FIG. 5, FIG. 7 is an enlarged diagram of region B of FIG. 3, FIG. 8 is an exploded perspective view of FIG. 7, and FIGS. 9 to 12 are reference diagrams for describing an operational mechanism of an automatic plunger pressurizing unit according to the exemplary embodiment of the present invention.

As illustrated in FIGS. 1 to 12, a drug injection device 1 according to the exemplary embodiment of the present invention comprises an ampoule holder portion 20 in which an ampoule M filled with an injectable solution is accommodated, a plunger 30 which is connected to the ampoule M and applies pressure to the injectable solution in the ampoule M, a manual plunger handle 100 which is connected to one side of the plunger 30 and manually applies pressure to the plunger 30, an automatic plunger pressurizing unit 200 which is selectively connected to the plunger 30 in a position adjacent to the plunger 30 and automatically applies pressure to the plunger 30 by means of power, a plunger guide body 300 which provides a plunger tunnel portion 310 guided while the plunger 30 is passed and is foldably attached to the automatic plunger pressurizing unit 200, and a protection casing 10 which protects the plunger guide body 300 and the automatic plunger pressurizing unit 200 at the outer sides of the plunger guide body 300 and the automatic plunger pressurizing unit 200.

First, referring to FIGS. 1 to 3, the protection casing 10 is a portion of forming the main body of the drug injection device 1 and accommodates a printed circuit board (PCB) 50 which is provided on the outer surface of the protection casing 10 and connected to an operational button 40 for controlling the automatic plunger pressurizing unit 200, in addition to the automatic plunger pressurizing unit 200, the plunger guide body 300, and a power supply portion 400 therein.

The protection casing 10 includes an upper casing 11 and a lower casing 12 separated from the upper casing 11. The upper casing 11 and the lower casing 12 are assembled with each other to be fixed by a clamping cap 13. In addition, a groove portion 13a which is dented in a circumferential direction is provided at the inside of the clamping cap 13, a projection portion P which is projected in the circumferential direction is provided at the outside of the front end of the upper casing 11 and the lower casing 12, and the projection portion P of the protection casing 10 engages with the groove portion 13a of the clamping cap 13.

Further, the protection casing 10 has two opened ends so that the plunger 30 may move through the inside of the protection casing 10. The ampoule holder portion 20 is detachably attached to the front opened end of the protection casing 10, and the manual plunger handle 100 is attached to the outer side of the protection casing 10.

In addition, a pusher switch 231b for selectively connecting and releasing the automatic plunger pressurizing unit 200 is provided on the upper surface of the upper casing 11, and an operational button 40 for operating the automatic plunger pressurizing unit 200 is provided on one surface to which the upper casing 11 and the lower casing 12 are attached.

In the exemplary embodiment, when an operator applies pressure to the pusher switch 231b which slides forward, the plunger 30 and the automatic plunger pressurizing unit 200 are connected to each other. When the operator applies the pressure to the pusher switch 231b which slides backward again, the plunger 30 and the automatic plunger pressurizing unit 200 are released from each other.

When the operator presses the operational button 40 while the plunger 30 and the automatic plunger pressurizing unit 200 are connected to each other, the automatic plunger pressurizing unit 200 operates. The detailed description there of will be described below for convenience.

The operational button 40 turns on/off the power supplied to the automatic plunger pressurizing unit 200, and further, serves to adjust an injection speed of the injectable solution (for example, different four-step injection speeds) step by step.

For example, in the exemplary embodiment, when the operational button 40 is pressed for a predetermined time or more and then detached, the injection speed of the injectable solution is adjusted step by step by the automatic plunger pressurizing unit 200. However, the scope of the present invention is not limited thereto, and in order to adjust the injection speed and the like step by step, a plurality of operational buttons 40 may be provided.

Although not illustrated, an LED lamp which displays a charging state of the battery 410, an automatic mode, and the injection speed may be provided at the side of the protection casing 10.

In the exemplary embodiment, the pusher switch 231b and the operational button 40 are provided on the outer wall of the protection casing 10, but for convenience of the operator, the operational button 40 may also be provided on one side of the manual plunger handle 100.

Meanwhile, a dental local anesthetic solution as the injectable solution of the exemplary embodiment is accommodated in the ampoule M. Although not illustrated in detail, the ampoule M is constituted by an ampoule body M1 having a pipe shape with two opened ends, a sealing cap M2 sealing one opening of the ampoule body M1, and a piston (not illustrated) sealing the other opening of the ampoule body M1 and movable along the inner wall of the ampoule body M1.

The ampoule holder portion 20 is detachably attached to the protection casing 10 and accommodates the ampoule M therein. The ampoule holder portion 20 includes an ampoule accommodation portion 23 which is accommodated with the ampoule M, a needle holder 22 which is attached to the ampoule accommodation portion 23, and an intra-injection needle 21 which is attached to the needle holder 22.

In the ampoule accommodation portion 23, the inside is hollow, a view port 23a which may verify the injectable solution remaining in the ampoule M is provided on the outer wall, the front end has a thread which is screw-attached to the needle holder 22, and the end portion is opened so that the ampoule M enters the inside. Further, the ampoule accommodation portion 23 includes a locking projection 23b which is projected from the outer wall of the end region of the ampoule accommodation portion 23.

As illustrated in FIGS. 4 to 6, the ampoule accommodation portion 23 is inserted to the protection casing 10 only in a direction in which a locking projection passing hole 13b formed in the clamping cap 13 is matched with the locking projection 23b so as to prevent the locking projection 23b of the ampoule accommodation portion 23 from interfering in the inlet of the clamping cap 13.

When the ampoule accommodation portion 23 is sufficiently inserted into the clamping cap 13, the end portion of the ampoule accommodation portion 23 faces an insert limiting wall B1 which is provided in the protection casing 10, and the ampoule accommodation portion 23 is not inserted at all. Next, when the ampoule accommodation portion 23 rotates forward and backward, the locking projection 23b interferes in an interference wall B2 of the protection casing 10 to prevent the ampoule accommodation portion 23 from being discharged outside the protection casing 10.

The needle holder 22 is detachably attached to the front end of the ampoule accommodation portion 23. In this case, the needle holder 22 is attached by connecting a thread of the front end of the ampoule accommodation portion 23 to a groove formed at the inside of the needle holder 22.

The intra-injection needle 21 passes through the sealing cap M2 of the ampoule M1 which is provided in the ampoule accommodation portion 23 through the needle holder 22 to communicate with the inside of the ampoule M. Accordingly, the injectable solution in the ampoule M is pressurized by the piston and injected to the person being operated on through the intra-injection needle 21.

Meanwhile, the piston is connected to a hook-shaped piston connection pin 31 which is attached to the front end of the plunger 30. The piston is provided with an elastic soft rubber material.

The piston connection pin 31 is inserted into the piston to prevent the piston and the plunger 30 from being separated from each other by the hook shape. Accordingly, even though the plunger 30 moves in a reverse direction of the direction of applying the pressure to the piston, the piston is not separated from the plunger 30 and pulled and moves in the reverse direction together.

The plunger 30 which reciprocates by applying the pressure to the piston operates by the manual plunger handle 100 or the automatic plunger pressurizing unit 200.

That is, when the injectable solution is injected to the person being operated on, the piston is pressurized by the plunger 30, and the plunger 30 is pressurized by the operation of the manual plunger handle 100 or the automatic plunger pressurizing unit 200 to eject the injectable solution accommodated in the ampoule M to the outside of the needle 21.

Hereinafter, the manual plunger handle 100 and the automatic plunger pressurizing unit 200 will be described in detail.

First, the manual plunger handle 100 is a configuration for manually operating the plunger 30 by the operator, and includes a handle gripping portion 110 for gripping the drug injection device 1 and a plunger pressurizing portion 120 for applying the pressure to the plunger 30.

The handle gripping portion 110 is attached to both sides of the protection casing 10 and provided in a shape of two circular closed-loops.

The handle gripping portion 110 includes a gripping portion body 111 forming an appearance, at least one insertion projection which is projected on two contact surfaces attached to two outer walls of the protection casing 10, and a passing hole 112 communicating with the protection casing 10 through the plunger 30.

In the handle gripping portion 110, as described above, the insertion projection 112 is inserted into the insertion grooves 11a and 12a which are formed on both sides of the protection casing 10 and the contact surface in a region communicating with the protection casing 10 is bolt-fastened and attached to the protection casing 10.

The plunger pressurizing portion 120 includes a ring-shaped pressurizing portion body 121 forming the appearance and a plunger connection pin 122 which connects the pressurizing portion body 121 and the plunger 30.

The pressurizing portion body 121 is adjacently shape-matched with the gripping portion body 111 to be provided to form three circular closed-loops together with the gripping portion body 111 with the protection casing 10 therebetween. However, the scope of the present invention is not limited thereto, and thus, the shapes of the pressurizing portion body 121 and the gripping portion body 111 may be designed and modified in various shapes.

The pressurizing portion body 121 is connected with the rear end of the plunger 30 which is exposed backward the protection casing 10 through the passing hole 113 of the handle gripping portion 110, by the plunger connection pin 122.

By using the manual plunger handle 100 having the configuration, the operator puts the index finger and the middle finger in the handle gripping portion 110 to grip the drug injection device 1. The operator may inject the injectable solution to the person being operated on by putting the thumb in the plunger pressurizing portion 120 to pull or push the plunger pressurizing portion 120 and moving the plunger 30 to manually apply the pressure to the piston of the ampoule M.

As described above, in the aspiration procedure, in the case where an injection time is relatively short due to a small amount of injectable solution and the person being operated on randomly determines that the injectable solution is injected according to sensitivity to patient's pain, it is convenient that the injectable solution is manually injected.

However, when the injectable solution is manually injected, the anesthetic solution is injected at a slow speed as possible in order to reduce the pain, but it is difficult for the operator to hold the drug injection device 1 for a long time at a predetermined injection speed.

In addition, when the operator is a woman, when the operator transfers sufficient pressure to the plunger 30, a hand-shaking phenomenon occurs or the injection speed is irregular to cause the pain to the person being operated on.

In order to compensate for the problem, the drug injection device 1 according to the exemplary embodiment is constituted by using manual and automatic injection methods and the automatic injection method is performed by the automatic plunger pressurizing unit 200. Hereinafter, the automatic plunger pressurizing unit 200 which operates in the protection casing 10 will be described in detail with reference to FIGS. 7 to 12.

The automatic plunger pressurizing unit 200 according to the exemplary embodiment includes a plunger driving portion 210 which is provide in the protection casing 10 and provides power for applying the pressure to the plunger 30, a connection gear portion 220 which is selectively connected to or released from the plunger 30 by a gear method, and a gear operating portion 230 which operates the connection gear portion 220.

In the exemplary embodiment, the connection gear portion 220 is constituted by a worm gear which is attached to the plunger driving portion 210 and a rack gear 222 which is formed on the outer surface of the plunger 20 to gear-engage with the worm gear 221.

The plunger driving portion 210 is provided as a driving motor 210 which rotates the worm gear 221 and the worm gear 221 is directly connected to a rotational shaft of the driving motor 210. In addition, the driving motor 210 and the worm gear 221 are integrally accommodated in a unit casing 240. The worm gear 221 engages with the rack gear 222 through a worm gear cut portion 241 for exposing the worm gear which is formed when the unit casing 240 is partially cut.

When the worm gear 221 rotates forward and backward by the driving motor 210, the rack gear 222 engaging with the worm gear 221 does not rotate, but straightly moves. Accordingly, while the plunger 30 which is integrally formed with the rack gear 222 straightly moves, the plunger 30 applies the pressure to the piston of the ampoule M.

Meanwhile, in the exemplary embodiment, the plunger 30 is provided to pass through the plunger guide body 300 including the plunger tunnel portion 310 which is guided while the plunger 30 is passed.

The plunger guide body 300 supports the unit casing 240 at the top and is foldably attached to the unit casing 240. In addition, the plunger guide body 300 and the unit casing 240 are connected to each other by a hinge pin (not illustrated) which forms the rotational shaft, and in this case, the plunger guide body 300 is fixed and the unit casing 240 is rotatable with respect to the plunger guide body 300.

In addition, the rack gear 222 formed in the plunger 30 may engage with the worm gear 221 through the rack gear cut portion 320 for exposing the rack gear which is formed when the plunger guide body 300 is partially cut.

The gear operating portion 230 includes a pusher 231 which operates the unit casing 240 while the worm gear 221 gear-engages with the rack gear 222 when slidely applying the pressure in one direction and an elastic member 232 which is connected to the unit casing 240 and elastically biased in a direction where the worm gear 221 is gear-released from the rack gear 222.

In the exemplar embodiment, the elastic member 232 may be a pair of springs. Of course, unlike the exemplar embodiment, the elastic member 232 may be replaced with various materials having elastic force.

The pusher 231 is constituted by a pressurizing member 231a which applies the pressure to the unit casing 240 (e.g., at surface 242) and a push switch 231b which is connected with the pressurizing member 231a by the pusher pin 231c.

The pusher switch 231b is exposed on the upper surface of the protection casing 10 to be pulled or pushed by the operator's fingers. Pressurizing force which is transferred from the pusher switch 231b is transferred to the pressurizing member 231a through the pusher pin 231c.

Figure 10:
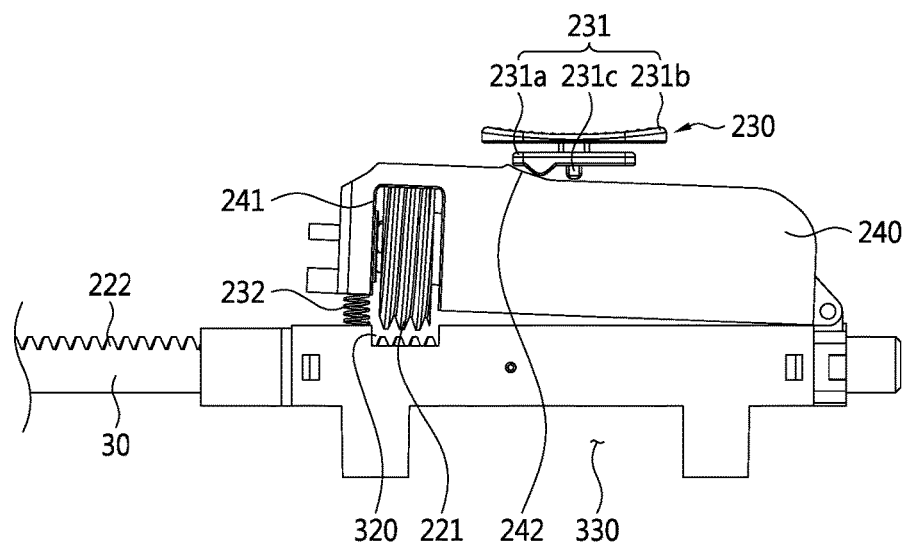
Figure 11:
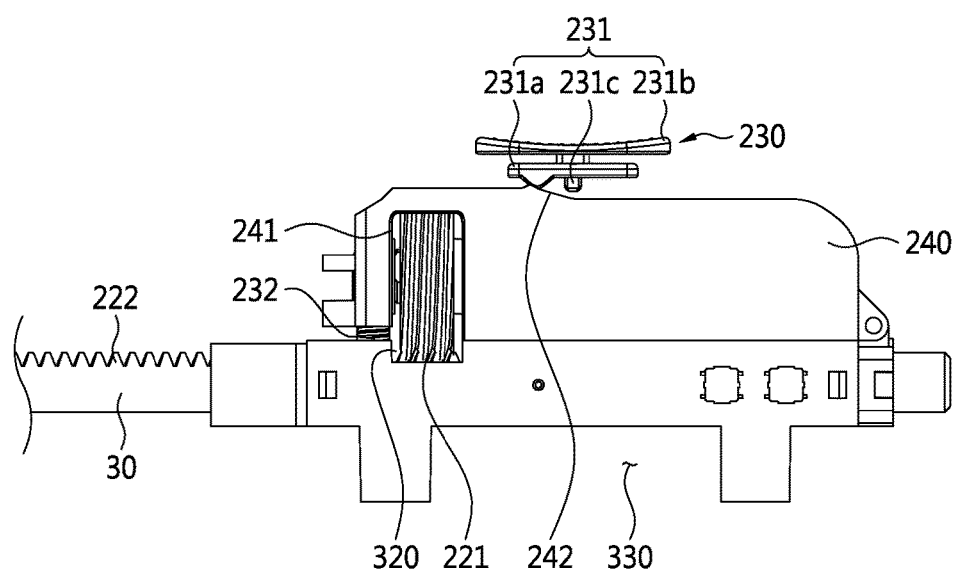
Figure 12:
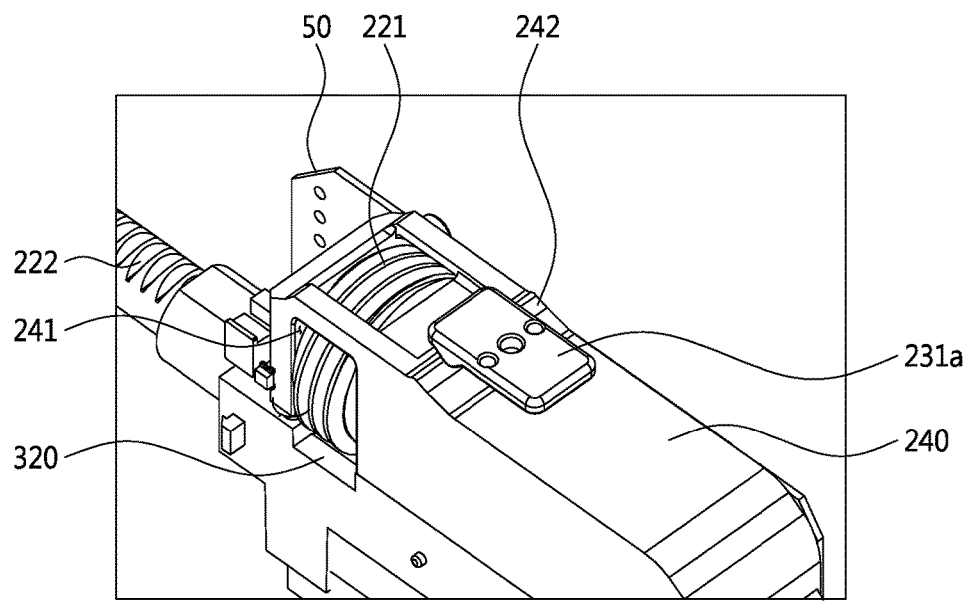

As illustrated in FIGS. 10 to 12, when the pressurizing member 231a slides forward along the slope contact portion which is formed on the upper surface of the unit casing 240, the unit casting 240 is pressurized to be folded to the plunger guide body 300. Accordingly, the elastic member 232 is compressed and the worm gear 221 and the rack gear 222 engage with each other.

On the contrary, when the pressurizing member 231a slides backward, while the elastic member 232 which is compressed between the unit casing 240 and the plunger guide body 300 is elastic-biased, the unit casing 240 and the plunger guide body 300 are spaced apart from each other, and as a result, the worm gear 221 and the rack gear 222 are released from each other.

By such a configuration, the operator pulls or pushes the pusher switch 231b which is provided on the upper surface of the protection casing 10 to connect and release the plunger 20 and the automatic pressurizing unit and may simply select the manual injection method and the automatic injection method.

Meanwhile, in the exemplary embodiment, the power supply portion 400 which supplies the power to the driving motor 210 is provided below the plunger guide body 300. To this end, the plunger guide body 300 further includes a power accommodation portion 330 having a barrier which is projected on the outer wall forming the bottom of the plunger guide body 300.

The power supply portion 400 includes at least one charging battery 410 supplying the power and a compliance module 420 which wirelessly charges the power in the charging battery 410. In addition, the compliance module 420 includes an RX coil portion 421 which receives induced current from external power and an RX_PCB 422 which is connected with the RX coil portion 421 and charges the current in the charging battery 410.

In the drug injection device 1 according to the exemplary embodiment, the power is charged in the charging battery 410 by a wirelessly charging method. When briefly describing the drug injection device 1, the drug injection device 1 may be mounted on a power charging cradle (not illustrated) in which a TX coil portion generating an electromagnetic field therein is included. In this case, the RX coil portion 421 receives the induced current generated from the TX coil portion. The induced current received from the RX coil portion 421 may be charged in the charging battery 410 through the RX_PCB 422.

Of course, in the exemplary embodiment, the wirelessly charging method is applied to the drug injection device 1 for convenience, but the scope of the present invention is limited thereto. Unlike the exemplary embodiment, the compliance module 420 may be configured to charge the charging battery 410 wiredly or electrically.

Hereinafter, an operation of the drug injection device 1 according to the exemplary embodiment of the present invention will be simply described.

First, the ampoule M accommodated with the injectable solution is inserted to the ampoule holder portion 20. Next, the ampoule holder portion 20 is inserted into the protection casing 10 in a direction where the locking projection passing hole 13b of the clamping cap 13 is matched with the locking projection 23b of the ampoule holder portion 20 to install the ampoule holder portion 20 in the protection casing 10.

In this case, the plunger pressurizing portion 120 is spaced apart from the handle gripping portion 110, and the plunger 30 of which one end is connected to the plunger pressurizing portion 120 is positioned to be exposed backward the protection casing 10.

Next, the operator selects and determines a more suitable injection method of the automatic injection method and the manual injection method if necessary.

The manual injection method and the automatic injection method may be easily switched by positioning the pusher switch 231b in an automatic mode or a manual mode as described above.

The manual injection method is similar to a general syringe injection method.

First, it is verified that the pusher switch 231b is positioned in the manual mode. Next, when the operator puts the index finger and the middle finger in the handle gripping portion 110 to easily grip the drug injection device 1 and puts the thumb in the plunger pressurizing portion 120 to push the plunger pressurizing portion 120 forward, the plunger 30 is pressurized, the plunger 30 applies the pressure to the piston of the ampoule M, and the piston applies the pressure to the injectable solution in the ampoule M, and the injectable solution is injected into an operation site through the intra-injection needle 21.

In addition, the automatic injection method is as follows.

First, the pusher switch 231b positioned in the manual mode slides forward to apply the pressure and then is positioned in the automatic mode. When the pusher switch 231*b* is positioned in the automatic mode, the unit casing 240 is folded with the plunger guide body 300, and the worm gear and the rack gear of the connection gear portion 220 engage with each other.

Next, when the operational button 40 positioned at the side of the protection casing 10 is pressed, the power is supplied to the driving motor 210 and the worm gear 221 which is directly connected to the driving motor 210 rotates. the rack gear 222 engaging with the worm gear 221 does not rotate, but slightly moves. Accordingly, the plunger 30 which is integrally formed with the rack gear 222 moves and applies the pressure to the piston of the ampoule M. The piston applies the pressure to the injectable solution in the ampoule M and the injectable solution is injected to the operation site through the intra-injection needle 21.

In this case, since the injectable solution is automatically injected into the body by the driving motor 210 at a predetermined speed, the person being operated on does not feel the pain.

Further, when the anesthetic state of the person being operated on is in progress enough not to largely feel the pain, the operator may rapidly adjust the automatic injection speed by manipulating the operational button 40 or rapidly inject the remaining injectable solution by switching the drug injection device to the manual mode.

As such, in the drug injection device according to the present invention, it is possible to enhance convenience by using the drug injection device manually and automatically and reduce a drug injection time by freely selecting an injection method according to sensitivity of a patient to improve satisfaction of the patient.

The present invention is not limited to the exemplary embodiments described herein, and it would be apparent to those skilled in the art that various changes and modifications might be made without departing from the spirit and the scope of the present invention. Accordingly, it will be determined that the changed examples or modified examples are included in the appended claims of the present invention.

INDUSTRIAL APPLICABILITY

The present invention relates to a drug injection device and can be used in medical industry, particularly, dental industry.

The invention claimed is:
1. A drug injection device comprising:
a plunger which is connected to an ampoule filled with an injectable solution and applies pressure to the injectable solution in the ampoule;
a manual plunger handle which is connected to one side of the plunger and manually applies pressure to the plunger; and
an automatic plunger pressurizing unit which is selectively connected to the plunger in a position adjacent to the plunger and automatically applies pressure to the plunger by means of power, wherein the automatic plunger pressurizing unit comprises:
a plunger driving portion which provides the power for applying the pressure to the plunger;
a connection gear portion which is selectively connected to or released from the plunger by a gear operating portion,
wherein the connection gear portion comprises:
a worm gear which is attached to the plunger driving portion; and
a rack gear which is formed on an outer surface of the plunger and directly engages with the worm gear, and
wherein the automatic plunger pressurizing unit further comprises a unit casing which integrally supports the plunger driving portion and the worm gear, and
wherein the gear operating portion comprises:
a pusher which operates the unit casing so that the worm gear engages with the rack gear when sliding pressure is applied in one direction; and
an elastic member which is connected to the unit casing and elastically biased in a direction in which the worm gear is released from the rack gear.

2. The drug injection device of claim 1, wherein the unit casing includes a slope contact portion formed on one surface facing the pusher, which is obliquely provided in a sliding direction of the pusher, and
the pusher comprises:
a pressurizing member which applies pressure to the unit casing while sliding along the slope contact portion; and
a pusher switch which is pin-connected to the pressurizing member.

3. The drug injection device of claim 1, wherein a worm gear cut portion for exposing the worm gear in which the worm gear is exposed is further formed in the unit casing.

4. The drug injection device of claim 1, further comprising:
a plunger guide body which provides a plunger tunnel portion guided while the plunger is passed and is foldably attached with the unit casing.

5. The drug injection device of claim 4, wherein a rack gear cut portion for exposing the rack gear in which the rack gear is exposed is further formed in the plunger tunnel portion.

6. The drug injection device of claim 4, further comprising:
a power supply unit which is accommodated in a power accommodation portion of the plunger guide body to supply power to the plunger driving portion,
wherein the power supply unit comprises:
at least one charging battery supplying the power; and
a compliance module which charges the at least one charging battery wiredly or wirelessly.

7. The drug injection device of claim 4, further comprising:
a protection casing which protects the plunger guide body and the automatic plunger pressurizing unit at the outer sides of the plunger guide body and the automatic plunger pressurizing unit.

8. The drug injection device of claim 7, wherein the manual plunger handle comprises:
a handle gripping portion which is attached to the outer wall of the protection casing to have a closed-loop shape and provided with a passing hole through which the plunger passes in a movement direction of the plunger; and
a plunger pressurizing portion which is connected to one end of the plunger through the passing hole and applies the pressure to the plunger.

9. The drug injection device of claim 8, wherein an insertion groove to which the handle gripping portion is inserted is formed on the outer wall of the protection casing and an insertion projection which is inserted to the insertion groove is provided on the handle gripping portion.

10. The drug injection device of claim 8, further comprising:

an ampoule holder portion which is accommodated with the ampoule of the injectable solution and inserted into the protection casing, wherein the ampoule holder portion comprises:

an ampoule accommodation portion in which the ampoule of the injectable solution is accommodated;

a needle holder which is attached to the ampoule accommodation portion; and an intra-injection needle which is attached to the needle holder, and the ampoule accommodation portion is provided with at least one locking projection which is projected in a circumferential direction in a position adjacent to the end portion of the ampoule accommodation portion, and when the ampoule accommodation portion rotates, the locking projection interferes in an interference wall formed in the protection casing.

11. The drug injection device of claim 10, wherein the protection casing comprises:

an upper casing; and a lower casing which is assembled with the upper casing, and a projection portion which is projected in a circumferential direction is provided at the upper casing and the outer side of the front end of the lower casing, the protection casing further comprises a clamping cap which clamps the upper casing and the lower casing, and a groove portion which is dented in a circumferential direction to engage with the projection portion is provided at the inside of the clamping cap.

* * * * *